United States Patent
DeMarch

(10) Patent No.: US 10,493,350 B2
(45) Date of Patent: Dec. 3, 2019

(54) BALANCE SENSORY AND MOTOR FEEDBACK MAT

(71) Applicant: Erica DeMarch, Denver, CO (US)

(72) Inventor: Erica DeMarch, Denver, CO (US)

(73) Assignee: Step and Connect, LLC, Denver, CO (US)

( * ) Notice: Subject to any disclaimer, the term of this patent is extended or adjusted under 35 U.S.C. 154(b) by 160 days.

(21) Appl. No.: 15/350,320

(22) Filed: Nov. 14, 2016

(65) Prior Publication Data

US 2017/0128816 A1 May 11, 2017

Related U.S. Application Data

(60) Provisional application No. 62/253,820, filed on Nov. 11, 2015.

(51) Int. Cl.
*A63B 71/06* (2006.01)
*G09B 19/00* (2006.01)
(Continued)

(52) U.S. Cl.
CPC .......... *A63B 71/0622* (2013.01); *A61B 5/112* (2013.01); *A61B 5/6892* (2013.01); *A63B 21/4037* (2015.10); *A63B 26/003* (2013.01); *A63B 71/06* (2013.01); *G09B 19/003* (2013.01); *G16H 20/30* (2018.01); *A61B 5/1117* (2013.01); *A61B 2505/09* (2013.01); *A63B 71/0009* (2013.01); *A63B 2071/0625* (2013.01); *A63B 2071/0647* (2013.01); *A63B 2071/0655* (2013.01); *A63B 2071/0694* (2013.01); *A63B 2209/10* (2013.01); *A63B 2220/52* (2013.01); *A63B 2220/53* (2013.01);
(Continued)

(58) Field of Classification Search
CPC ........................ A63B 71/0622; A63B 71/0625
See application file for complete search history.

(56) References Cited

U.S. PATENT DOCUMENTS

| 127,376 A | 5/1872 | Sloan | |
|---|---|---|---|
| 5,066,000 A * | 11/1991 | Dolan | A63B 23/0464 472/90 |

(Continued)

FOREIGN PATENT DOCUMENTS

| JP | 5692929 | 4/2015 |
|---|---|---|
| WO | WO 87/01574 | 3/1987 |

(Continued)

OTHER PUBLICATIONS

"Balance Matters" accessible in 2018 and printed from URL <https://stepandconnect.com/Balance-Matters> on Jul. 29, 2019, 7 pages.*

(Continued)

*Primary Examiner* — Jason Skaarup
(74) *Attorney, Agent, or Firm* — Lewis Brisbois Bisgaard & Smith LLP; Craig W Mueller

(57) ABSTRACT

A therapy system combining sensory input configured to enhance patients balance and stepping is provided. The system may include a mat that selectively receives a plurality of targets. The targets are contacted by the patient's feet and return an audible signal. The system allows a healthcare professional or patient to analyze gait and balance, and correct the same if needed.

18 Claims, 8 Drawing Sheets

(51) Int. Cl.
| | |
|---|---|
| *A63B 26/00* | (2006.01) |
| *A63B 21/00* | (2006.01) |
| *A61B 5/00* | (2006.01) |
| *A61B 5/11* | (2006.01) |
| *G16H 20/30* | (2018.01) |
| *A63B 71/00* | (2006.01) |
| *G16H 40/63* | (2018.01) |

(52) U.S. Cl.
CPC ..... *A63B 2220/56* (2013.01); *A63B 2225/093* (2013.01); *A63B 2225/50* (2013.01); *G16H 40/63* (2018.01)

(56) References Cited

U.S. PATENT DOCUMENTS

| | | | |
|---|---|---|---|
| 5,096,188 | A | 3/1992 | Shen |
| 5,118,112 | A | 6/1992 | Bregman et al. |
| 5,476,103 | A | 12/1995 | Nahsner |
| 5,551,445 | A | 9/1996 | Nashner |
| 5,574,669 | A * | 11/1996 | Marshall ............ A63B 71/0686 702/149 |
| 5,642,880 | A | 7/1997 | Wiseman et al. |
| 5,803,835 | A * | 9/1998 | Moton .................... A63B 5/22 473/414 |
| 5,839,976 | A * | 11/1998 | Darr ........................ A63B 5/22 473/414 |
| 5,929,332 | A | 7/1999 | Brown |
| 5,971,761 | A * | 10/1999 | Tillman, Sr. ............. G09B 5/06 434/159 |
| 6,010,465 | A | 1/2000 | Nashner |
| 6,102,818 | A | 8/2000 | Hamilton |
| 6,405,606 | B1 | 6/2002 | Walczyk et al. |
| 6,450,886 | B1 | 9/2002 | Yamano et al. |
| 7,004,895 | B2 | 2/2006 | Perry et al. |
| 7,191,644 | B2 | 3/2007 | Haselhurst et al. |
| 7,955,224 | B2 | 6/2011 | Curley |
| 8,235,870 | B2 | 8/2012 | Hamilton |
| 8,702,567 | B2 | 4/2014 | Hu et al. |
| 8,900,165 | B2 | 12/2014 | Jeka et al. |
| 9,084,712 | B2 | 7/2015 | Roerdink et al. |
| 9,211,437 | B2 | 12/2015 | Soba |
| 2003/0009308 | A1 | 1/2003 | Kertley |
| 2004/0009845 | A1 | 1/2004 | Johnson |
| 2004/0043336 | A1 | 3/2004 | De Ponnat et al. |
| 2004/0043362 | A1 | 3/2004 | Aughenbaugh et al. |
| 2004/0043363 | A1 | 3/2004 | Dorner et al. |
| 2004/0043364 | A1 | 3/2004 | Wasowicz |
| 2004/0043365 | A1 | 3/2004 | Kelley et al. |
| 2004/0043366 | A1 | 3/2004 | Stoneberg |
| 2004/0043367 | A1 | 3/2004 | Chou |
| 2004/0043368 | A1 | 3/2004 | Hsieh et al. |
| 2004/0043369 | A1 | 3/2004 | Pawar et al. |
| 2004/0214692 | A1 | 10/2004 | Koenig |
| 2005/0048871 | A1 | 3/2005 | Brown |
| 2005/0170935 | A1 | 8/2005 | Manser |
| 2006/0154220 | A1 | 7/2006 | Toniolo |
| 2007/0255186 | A1 | 11/2007 | Grill |
| 2007/0298937 | A1 | 12/2007 | Shah et al. |
| 2008/0066343 | A1 | 3/2008 | Sanabria-Hernandez |
| 2009/0062076 | A1 * | 3/2009 | Curley ................... A63B 26/00 482/23 |
| 2010/0016125 | A1 * | 1/2010 | Bellandi ................. A63B 6/00 482/4 |
| 2011/0184225 | A1 | 7/2011 | Whitall et al. |
| 2011/0195392 | A1 * | 8/2011 | Kim ........................ G09B 19/00 434/365 |
| 2012/0289866 | A1 | 11/2012 | Irby et al. |
| 2013/0180048 | A1 | 7/2013 | Saltzman |
| 2013/0181907 | A1 | 7/2013 | Russell et al. |
| 2014/0152450 | A1 | 6/2014 | Hjort et al. |
| 2015/0080181 | A1 | 3/2015 | Skulman |
| 2015/0301643 | A1 | 10/2015 | Hafidh et al. |
| 2015/0364059 | A1 | 12/2015 | Marks et al. |

FOREIGN PATENT DOCUMENTS

| | | |
|---|---|---|
| WO | WO 01/08755 | 2/2001 |
| WO | WO 0136051 | 5/2001 |
| WO | 2013027145 A2 | 2/2013 |

OTHER PUBLICATIONS

"Summary of the Updated American Geriatrics Society/British Geriatrics Society clinical practice guideline for prevention of falls in older persons," Panel on Prevention of Falls in Older Persons, American Geriatrics Society and British Geriatrics Society, J Am Geriatr Soc, 2011, vol. 59(1), pp. 148-157.

Bennell et al., "Intra-rater and Inter-tester reliability of a weightbearing lunge measure of ankle dorsiflexion," Australian Physiotherapy, 1998, vol. 24(2), pp. 211-212.

Bretan, "Plantar cutaneous sensitivity as a risk for falls in the elderly," Rev. Assoc. Med. Bras., 2012, vol. 58(2), pp. 132.

Casamassima et al., A Wearable System for Gait Training in Subjects with Parkinson's Disease Sensors (Basel), 2014, vol. 14(4), pp. 6229-6246.

Cho et al., "Tests of stepping as indicators of mobility, balance, and fall risk in balance-impaired older adults," J Am Geriatr Soc., 2004, vol. 52, pp. 1168-1173.

Duncan et al., "Functional reach: a new clinical measure of balance," J Gerontol biol Sci Med Sci, 1990, vol. 45, pp. M192-M197.

Galna et al., "Obstacle crossing in people with Parkinson's disease: foot clearance and spatiotemporal deficits," Hum. Movement Sci., 2010, vol. 29, pp. 843-852.

Golderberg et al., "Concurrent Validity and Reliability of the Maximum Step Length Test in Older Adults," Journal of Geriatric Physical Therapy, 2010, vol. 33, pp. 122-127.

Gosselin et al., "Foam pads properties and their effects on posturography in participants of different weight," Chiropractic & Manual Therapies, 201523:2.

Hatton et al., Standing on textured surfaces: Effects on standing balance in healthy older adults, Age Ageing, 2011, vol. 40, pp. 363-368.

Hausdorff, "Gait dynamics, fractals and falls: Finding meaning in the stride-to-stride fluctuations of human walking," Hum. Mov. Sci.,2007, vol. 26, pp. 555-589.

Horak et al., "Role of Body-Worn Movement Monitor Technology for Balance and Gait Rehabilitation," Phys. Ther., 2015, vol. 95(3), pp. 461-470.

Horak, "Postural orientation and equilibrium: what do we need to know about neural control of balance to prevent falls?" Age and Ageing, 2006, vol. 35-S2.

King et al., "Delaying Mobility Disability in People with Parkinson Disease Using a Sensorimotor Agility Exercise Program," Physical Therapy, 2009, vol. 89(4), pp. 384-393.

König et al., "Can Gait Signatures Provide Quantitative Measures for Aiding Clinical Decision-Making? A Systematic Meta-Analysis of Gait Variability Behavior in Patients with Parkinson's Disease," Frontiers in Human Neuroscience, 2016, vol. 10(319), ___ pages.

Königa et al., "Revealing the quality of movement: A meta-analysis review to quantify the thresholds to pathological variability during standing and walking," Neuroscience & Biobehavioral Reviews, 2016, vol. 68, pp. 111-119.

Krause et al., Measurement of ankle dorsiflexion: a comparison of active and passive techniques in multiple positions.

Lesinski et sl., "Effects of Balance Training on balance Performance in Healthy Older Adults: A Systematic Review and Meta-analysis," Sports Medicine, 2015, vol. 45, pp. 1721-1738.

Lin et al., "Test-retest reliability of postural stability on two different foam pads," Journal of Nature and Science, 2015, vol. 1(2), p. e43.

Maki et al., "Effect of facilitation of sensation from plantar foot-surface boundaries on postural stabilization in young and older adults," J Gerontol, 1999, vol. 54A, pp. M281-M287.

Menz et al., "Foot and ankle characteristics associated with impaired balance and functional ability in older people," J Gerontol A BiolSci Med Sci, 2005, vol. 60A, pp. 1546-1552.

(56) References Cited

OTHER PUBLICATIONS

Moncada, "Review Management of falls in older persons: a prescription for prevention," am Fam Physician, 2011, vol. 84(11), pp. 1267-1276.
Orth et al., "The Role of Textured Materials in Supporting Perceptual-Motor Functions," Plosone, 2013, vol. 8(4), pp.
Palluel et al., Do spike insoles enhance postural stability and plantar-surface cutaneous sensitivity in the elderly?, Age, 2008, vol. 30, pp. 53-61.
Park et al., "What is Wrong with Balance in Parkinson's Disease?" Journal of Movement disorders, 2015, vol. 8(3), pp. 109-114.
Preszner-Domjan et al., "When does mechanical plantar stimulation promote sensory re-weighing: Standing on a firm or compliant surface?" Eur J Appl Physiol, 2012, vol. 112, pp. 2979-2987.
Plúčik et al., "Assessment of Visual Reliance in Balance Control: An Inexpensive Extension of the Static Posturography," Journal of Medical Engineering, 2014, vol. 2014, 9 pages.
Robinovitch et al., "Video capture of the circumstances of falls in elderly people residing in long-term care: An observational study," the Lancet, 2013, vol. 381, pp. 47-54.
Rossi et al., "The effects of a perturbation-based balance training on the reactive neuromuscular control in community-dwelling older women: a randomized controlled trial," Hum. Mov., 2013, vol. 14(3), pp. 238-246.
Sherrington et al., "Exercise to prevent falls in older adults: an updated meta-analysis and best practice recommendations," N S W Public Health Bull., 2011, vol. 22(3-4), pp. 78-83.
International Search Report and Written Opinion for International (PCT) Patent Application No. PCT/US2016/061782, dated Jan. 23, 2017, 11 pages.
Supplementary European Search Report for EP16865191, dated Jun. 11, 2019. 11 Pages.

* cited by examiner

BALANCE SENSORY AND MOTOR FEEDBACK MAT

This application claims the benefit of U.S. Provisional Patent Application Ser. No. 62/253,820, filed Nov. 11, 2015, the entirety of which is incorporated by reference herein.

FIELD OF THE INVENTION

Embodiments of the present invention generally relate to exercise equipment that provides sensory and motor feedback to assess and improve balance and stepping. One embodiment is a mat used to train gait mechanics, process sensory (visual, somatosensory, and vestibular) responses; and implement motor equilibrium strategies (ankle, hip, and stepping). The contemplated mat can be used for people of all ages and abilities, including those with neurological disorders (Parkinson's disease, Multiple Sclerosis, traumatic brain injury, stroke, etc.), neuropathies from diabetes or from chemotherapy, lower extremity joint replacements, or prosthetics post amputation.

BACKGROUND OF THE INVENTION

Individuals suffering from a neurological disorder often must relearn to walk. Improving walking ability is critical to rehabilitation. Often, the initial stages of therapy begin with evaluating the patient's balance and gait to assess their fall risk. After a neurological incident, experts also recommend balance and gait be assessed and corrected by training if necessary. Studies have shown that incorrect weight shifting, e.g., leaning too far forward during standing or walking, improper foot placement during walking, etc., is the most frequent cause of falling, encompassing 41% of falls. Fall prevention and exercising is also important for elderly individuals as, according to the Center for Disease Control, one out of three older people fall each year. Older adults and persons with neurological disorders such as Parkinson's disease, Multiple Sclerosis, stroke, and peripheral neuropathy have gait impairments and, thus, are at a higher risk of falling. These individuals require repetitive stepping and gait mechanics training.

Patients initially use rehabilitation products under a therapist's supervision. After discharge, the patient is expected to continue the prescribed therapy at home. Current balance and gait training products used in clinics are often not affordable for some clinics or for clients to buy for home use. It follows that some patients cannot follow the prescribed treatment protocol because the tools needed are not portable and available for home use. Further, patients trying to perform stepping and balance exercises at home also often lack the appropriate feedback and require guidance to ensure they are performing the prescribed exercises correctly Another related drawback of prior art devices is that they are difficult to set up and use correctly. The more complex the device is to set up, especially for impaired individuals or non-professionals, correct and consistent use will decrease, which will decrease the therapy's effectivity. That is, patients need continued practice with good form and training to maintain their current level of progress or continue to improve on the progress they have made during professionally-conducted therapy. Experts have advised that balance training be conducted permanently to contract age-related declines in balance performance. The need for an easy to use system is paramount to encourage patients or individuals struggling with motor issues to continue their training and therapy.

There are many types of exercise equipment that aim to improve balance, proprioception, and sensory processing, but they do not provide both balance and gait training and cannot be used both in the clinic and in a patient's home. For example, some prior art devices provide square or circle shaped force plates that accommodate a single foot. These devices cannot incorporate all the gait phases, train gait mechanics, and adapt balance to different surfaces and textures. That is, prior art devices that simply provide force plates do not address walking from one surface to another at various heights and surface densities.

For example, proprioception (joint position) machines are disclosed in U.S. Pat. No. 7,004,895 to Perry et al. This machine perturbs in all directions for reactive balance but does not train voluntary balance needed for stepping during gait. It also does not allow feedback for proprioception of the hip during gait for step length, width, or height or at the ankle/foot for a smooth transition heel to toe to negotiate all terrains and over obstacles.

In addition, balance products manufactured by NeuroCom International, Inc. (See, for example, U.S. Pat. Nos. 5,476,103, 5,551,445, and 6,010,465, measure an individual's balance task performance and use force-plates on which a patient stands to record changes in the position of the center of force exerted by the feet against the support surface. Gait mechanics and stepping more than one step is not possible with these devices. NeuroCom's products do not use textured materials in the shape of a footprint to provide more accurate feedback for stepping, which we described in further detail below. Alternatively, feedback provided for center of force changes is provided on a screen, which is not ideal.

Many balance systems such as the Wii Fit® produced by Nintendo® or Balance Master® produced by Natus® primarily provide visual feedback received from an underfoot force plate and do not stimulate the mechanoreceptors in the feet. These products also fail to provide a closed-loop feedback when the patient's eyes are closed or their head is turned to challenge the vestibular system.

WO2001008755 to Ganville et al. discloses targets laid out grids (15 cm squares). The target pads are pressure sensitive but not shaped as a footprint with increased sensitivity to width, height, and length. The disclosed device also does not provide textured targets. Further, as the disclosed invention is more suitable for gait mechanics from heel contact to forefoot (loading response), the grid targets cannot determine location of both foot and heel contact. Lunges can hit the target but, again, are one-dimensional with only small sensitivity for width, and step height is not addressed. Although the lamina, e.g., the mat, may also have different textured surfaces for the user to perform the exercises on, the textures are not in the shape of a footprint and do not provide step position feedback. U.S. Pat. No. 8,900,165 to Jeka is directed to a balance training system for improving a user's postural control by providing visual feedback regarding the user's center of mass (CoM) via a display.

U.S. Patent Application Publication No. 2015/0364059 to Marks et al. is directed to an exercise mat that includes sensors that provide real-time feedback using visual and auditory systems to correct weight distribution of yoga poses. It provides no tactile feedback and does not contemplate training gait mechanics.

Health care professionals often use visual cues such as laser lights (see, for example, U.S. Patent Application Publication No. 2007/0255186 and U.S. Pat. Nos. 8,702,567 and 9,084,712), and/or tape marks positioned on the floor to provide step or gait training feedback. These methods can help increase step length, but can detrimentally increase patient dependence on visual cues for balance. Further, these methods often force the patient to look down, which results in poor posture and decreased integration of their vestibular system. Research shows older adults and people with Parkinson's disease over rely on their visual system for balance. Visual reliance/dependence can increase an individual's fall risk in visually stimulating environments, when turning one's head, or dark areas.

WO1987001574A1 to Bugarini discloses a system that allows a walkway to be scanned in real-time during a patient's gait analysis at a sampling frequency higher or equal to 50 Hz, and distributing the support pressures exerted by the sole of the feet to be determined in a full gait cycle (double step). Bugarini provides a walkway of sufficient size to measure double step and evaluate the foot pressures, but does not allow treatment protocols to improve gait mechanics, challenge the sensory systems, provide sensory re-weighting and adapt balance to different surfaces and heights. This system is not for a patient to use at home.

U.S. Patent Application Publication No. 2011/0184225 to Whitall relates to training step length and step rate ratio for a given velocity in response to a rhythmic auditory cue which allows spatial and temporal gait parameters and gait speed can be actively changed. Although this device provides step length feedback through auditory cues, it does not incorporate the foot/ankle mechanics and heel toe rocker movement. For example, a patient can step with a flat foot and it could not provide feedback to change the gait mechanics.

The prior art also includes boards/mats that attempt to improve step length with varied heights. For example, U.S. Patent Application Publication No. 2004/0009845 to Johnson uses a gait board for inside parallel bars to assist step length and height using hurdles, but does not incorporate textured foot prints for foot placement and use of auditory cues for improved initial contact and loading response. A patient can take a large step over a hurdle and with a flat foot which does not coincide with a normal gait.

JP5692929B2 to Aoyama describes an exercise mat that is supposed to prevent falling. The mat has an upper walking surface that includes a color-coded pattern that includes at least two or more different colors, which relies on the visual system for balance with decreased integration of the somatosensory and vestibular system. This mat's aim is to improve gaze behavior requiring patients to look down using this mat for proper stepping rather than stepping to a textured target or auditory feedback for proper gait mechanics. This mat also fails to provide a closed-loop feedback when the patient's eyes are closed or their head is turned to challenge the vestibular system.

U.S. Patent Application Publication 2004/0214692 to Koenig discloses an exercise mat having a grid composed of intersecting straight lines and sequential reference indicia. The grid lines and marks can be a different colors, thicknesses, and types (such as dashed lines), and can have a convex or concave protrusion associated with the surface of the exercise mat that differentiates one mark from another. The grid lines may also assist in exercise alignment, to measure stretching progress from one week to another week, or to identify correct dance movements. Koenig's mat relies on visual cues for step position does not provide the feedback needed for gait or incorporate textures and foam to train the somatosensory and vestibular systems. Feedback on step position with progressions with head turns or eyes closed cannot be performed on Koenig's mat due to the user must look down for feedback if they are in correct position.

U.S. Patent Application Publication No. 2013/0180048 to Saltzman generally relates to an exercise yoga mat, where the mat has printed indicia for measuring distance along the surface of the mat.

U.S. Pat. No. 5,096,188 to Shen discloses a device for magnetic therapy and foot massage. Although interchangeable pebble-like convex moldings can be arranged along the board, the moldings are not in the shape of a foot and cannot be used for foot placement to determine limb position (proprioception) and for gait mechanics. It also does not incorporate different foam densities to challenge the vestibular system or provide sensory re-weighting (stepping from one texture surface to another).

U.S. Patent Application Publication No. 2005/0170935 to Manser provides an exercise surface for increasing the proprioceptive demands on the foot, ankle, and lower leg. The exercise surface includes a plurality of projections extending upward therefrom, and is adapted for use as an exercise mat or a treadmill belt. The textured surfaces may challenge a person's proprioception but it does not provide feedback for foot placement position (step length, width, or height) or proper gait mechanics at initial contact and push-off Manser does not include varied foam densities to challenge the vestibular system as he is only challenging the somatosensory system (proprioception) His art also does not allow training for sensory re-weighting for postural control, adapting from changing environmental conditions and available sensory information (i.e. hard surface—somatosensory to foam-vestibular)

U.S. Pat. No. 7,955,224 and U.S. Patent Application Publication No. 2009/0062076 to Curley is directed to a yoga mat with hand and feet placement stations that provide tactile and audio feedback. Curley was designed to assist visually impaired to perform yoga poses and does not address gait mechanics or integration of all the balance systems. Further, Curley does not include varied heights and foam densities to challenge the vestibular system or provide sensory re-weighting for postural control U.S. Pat. No. 9,211,437 to Soba teaches a yoga and exercise mat with attachable markers. The markers are affixed to the mat and help yoga performers or exercisers maintain a proper posture, enhance their physical form, achieve desired positioning, and to greatly minimize a potential safety hazard and the risk of injury. In particular, the attachable markers are manufactured in an array of different shapes, styles, and colors to aide visually impaired individuals. Soba, however, does not teach the use of markers that provide tactile or auditory feedback.

U.S. Patent Application Publication No. 2008/0066343 to Sanabria-Hernandez is directed to an invention that helps mitigate "toe-walking" and or "heel-walking" by training; namely by prompting an auditory stimulus as positive reinforcement when pressure is placed on an inappropriate portion of the foot. Step length, sensory processing, and re-weighting to different surfaces, etc. is not measured or could be trained U.S. Pat. No. 5,929,332 to Brown discloses a sensor for monitoring the condition of strike force a foot within a shoe. More specifically, Brown provides a computerized foot pressure microcomputer that receives signals from sensors and analyzes them to determine if a critical situation exists regarding whether sufficient foot pressure is applied by a walking patient. Similarly, U.S. Patent Application Publication No. 2003/0009308 to Kertley is directed to a combination of sensors in a shoe sole wherein data from the sensors is stored and relayed to a monitoring assessment for determining running/walking cadence of a test subject. These inventions do not combine sensory input to enhance balance and stepping.

Additionally, U.S. Pat. No. 6,405,606 to Walczyk et al. is directed to a shoe system that provides biofeedback relating to a gait vector. This reference discloses the combination of a gait and forced sensor and provides some physical measurement to measure a patient's force placed upon an injured limb during use. In an additional example, some children's footwear may provide auditory stimulus when the child places pressure on a heel portion of a sandal, the auditory stimulus is made by a simple squeaky-air pressure type mechanism for entertainment (generating a "squeak-sound").

U.S. Pat. No. 7,191,644 to Haselhurst teaches a gait system designed to assist with the treatment of subjects with a lack of sensation due to nerve damage or amputation. Such individuals are often unable to tell when their foot contacts the floor. The system includes a removable insole placed inside the shoe which proportionally senses touchdown of the limb.

WO2001036051 to Avni teaches an adaptive weight bearing monitoring system for rehabilitating injuries affecting the mobility of a lower limb of a patient. At least one set of sensor units detects weight forces applied to at least two monitored locations of at least one limb. The sensors generate dynamic weight input signals from each of said monitored locations. Much like the references described herein related to footwear, this reference is irrelevant to a mat that provides biofeedback to a patient or therapist assessing gait and balance.

Further, there are also many products designed to help foot position, stance, and stride for athletes especially in golf, baseball, and dancing. None include training for proper gait mechanics and sensory processing. For example, U.S. Patent Application Publication No. 2006/0154220 to Toniolo is a dance training device that helps teach individuals proper foot position and body movement. The training device allows the individual to determine the correct position of his or her feet in relation to a ballet bar.

U.S. Pat. No. 6,102,818 to Hamilton is directed to an athletic training device for teaching proper baseball hitting, throwing, and fielding techniques. The mat includes positional indicia that indicate proper stance and stride positions. One side of the mat has positional indicia for teaching proper technique for hitting. U.S. Pat. No. 5,642,880 to Wiseman teaches a similar device with pressure sensitive areas for temporarily indicating the position of the batter's feet after they swing the bat.

U.S. Pat. No. 5,118,112 to Bregman teaches a system for analyzing golfer balance and weight shifts from one foot to the other and between the heel and toe of each foot during a golf swing. The disclosed system generally comprises two foot pads capable of measuring weight on each pad and on the front and rear portions of each pad, a display, a sound sensor for sensing the impact of a golf club against a golf ball, and a microprocessor system for receiving information from the pads and generating the display. The results may be used by the golfer to adjust his swing toward the optimum.

Finally, U.S. Patent Application Publication No. 2004/004336 to Chou provides a dancing machine that includes a base that has stepped stages wherein each of the two-step stages has a plurality of step on pads. A single unit is located on the front of the base as provide lights, music, and a display that shows the number of calories burned. Chou's dancing machine does not combine sensory inputs to enhance balance, stepping and proper gait mechanics.

While the prior art mentioned hereinabove teaches various forms of yoga and exercise mats with distinct functionalities, they do not measure step length and width for gait.

Increased gait variability predicts falls among community-living older adults and those with neurological diagnoses. This invention intends to address this issue to improve symmetry of stepping. The following articles provide additional insight related to balance and gait issues faced by some neurological patients:

Jozef Púčik, Marián Šaling, Tomáš Lukáč, Oldřich Ondráček, and Martin Kuchařík, "Assessment of Visual Reliance in Balance Control: An Inexpensive Extension of the Static Posturography," Journal of Medical Engineering, vol. 2014, Article ID 248316, 9 pages, 2014. doi:10.1155/2014/248316.

John J. Jeka, Leslie K. Allison, and Tim Kiemel. The Dynamics of Visual Reweighting in Healthy and Fall-Prone Older Adults. Journal of Motor Behavior Vol. 42, Iss. 4, 2010.

Park J-H, Kang Y-J, Horak F B. What Is Wrong with Balance in Parkinson's Disease? Journal of Movement Disorders. 2015; 8(3): 109-114. doi:10.14802/jmd.15018.

Fay Horak. Postural orientation and equilibrium: what do we need to know about neural control of balance to prevent falls? Age and Ageing 2006; 35-S2.

King L A, Horak F B. Delaying Mobility Disability in People with Parkinson Disease Using a Sensorimotor Agility Exercise Program. Physical Therapy. 2009; 89(4): 384-393. doi:10.2522/ptj.20080214.

B. Galna, A. T. Murphy, M. E. Morris, Obstacle crossing in people with Parkinson's disease: foot clearance and spatiotemporal deficits, Hum. Movement Sci. 29 (2010) 843-852.

Hausdorff, J. M. (2007) Gait dynamics, fractals and falls: Finding meaning in the stride-to-stride fluctuations of human walking. Hum. Mov. Sci., 26, 555-589.

N. Königa, 1, W. R. Taylora, 1, C. R. Baumannb, N. Wenderothc, N. B. Singha Revealing the quality of movement: A meta-analysis review to quantify the thresholds to pathological variability during standing and walking. Neuroscience & Biobehavioral Reviews Volume 68, September 2016, Pages 111-119.

Konig N, Singh N B, Baumann C R, Taylor W R. Can Gait Signatures Provide Quantitative Measures for Aiding Clinical Decision-Making? A Systematic Meta-Analysis of Gait Variability Behavior in Patients with Parkinson's Disease. Frontiers in Human Neuroscience. 2016; 10:319. doi:10.3389/fnhum.2016.00319.

It is a long-felt need to provide a training mat that is portable, easy to use, affordable, and that addresses many of the prior art drawbacks. Embodiments of the invention described herein were developed to help people reach their fullest potential by achieving individual goals and preventing falls. A science-based approach combined with a clinical need led to the development of a feedback mat to assess and train step position, gait symmetry, and mechanics. The portable mat disclosed herein also allows therapists to evaluate and specifically train the appropriate balance system (the visual, the somatosensory, and/or the vestibular system), that can be easily applied in the clinic or the patient's home.

SUMMARY OF THE INVENTION

It is one aspect of some embodiments of the present invention to provide a mat that allows the selective placement of foot targets so patients are aware of exact foot placement for a prescribed exercise. The targets may be selectively interconnected to the mat. Further, the targets may have a texture that is different from that of the mat. Still further, the targets may emit an auditory signal when touched by the patient's foot. This functionality also allows patients to assess their progress associated with larger steps or balancing with their feet closer together.

It is another aspect of embodiments of the present invention to provide a mat that include sensory (e.g., cutaneous, proprioceptive, kinesthetic, and auditory) feedback for better integration of the patient's balance systems (visual, somatosensory, and vestibular), equilibrium strategies (ankle, hip, and stepping), and gait mechanics. Embodiments of the present invention achieve this goal by employing targets that provide somatosensory feedback to smooth out forward progression over the foot. The targets may be shaped as a footprint, bottom of the shoe, circular, triangular, square, or any combination thereof.

It is a related aspect of some embodiments of the present invention to provide selectively positionable targets. Here, the therapist can position the targets on the mat to vary their orientation to and length and width between targets, which will dictate gait length and width. The mats of some embodiments of the present invention may include loop strips that selectively receive a complementary hooked surface of the target. A tape measure printed on an edge of the mat may also be provided, which allows selective positioning of the interchangeably textured targets. This functionality also allows for assessment and treatment of step length and gait width, which allows for progression monitoring.

It is another aspect of embodiments of the present invention to provide a mat that provides biofeedback to the therapist or patient. Biofeedback provides therapists with a useful tool for giving patients quick, precise instructions on how to modify their movement. Some embodiments of the present invention incorporate real-time feedback related to motor performance through textured targets and/or auditory cues issued by the targets that use signals from the patient's body to improve neural-motor performance. Those of ordinary skill in the art will appreciate motor learning through augmented sensory information has been used with success in rehabilitating and exercising gait, step, and dynamic repetitive movements. Using external cues, such as rhythmic auditory stimulation (RAS) has also appeared to enhance motor performance in the context of stepping in gait. Studies involving RAS are based on open-loop systems, i.e., the cues are administered without considering the actual performance of the patient in real-time.

Embodiments of the present invention deviates from many prior art devices that use open-loop approaches, e.g., feedforward responding to a movement reference, to a closed-loop approach, which includes feedback and contemplates responding to information about movement performance. The closed-loop approach also attempts to decrease reliance on the patient's visual system to enhance gait and balance, which is achieved by using the textured footprints. When a patient steps onto a textured target, which is described in detail below, they can tacitly assess whether they have reached the target or if they are short, long, left, or right of the target. Auditory cues emitted by targets of some embodiments of the present invention, also provides immediate feedback with positive reinforcement of the patient's neural-motor performance. The auditory cue of one embodiment of the present invention is a click. Those of ordinary skill the art will appreciate that other auditory cues could be used, such as beepers, bells, buzzers, or similar sound-producing devices or mechanisms. Separate auditory cues at the heel and the forefoot target portions may be provided, which will improve step symmetry, allow fewer verbal cues, allow more efficient patient mental processing, and provide feedback associated with gait mechanics for heel contact and push off.

The target, i.e., footprints, provided by some embodiments of the present invention incorporate means to produce tactile sensations by employing various textures. Upon contact with the patient's foot, the target texture produces feedback which improves balance system and gait mechanics integration. One advantage of using textured surfaces involves facilitating tighter regulation and control of spatial and temporal characteristics of the patient's center of mass. Improvements in the ability to detect information changes, such as changes in balance or limb positioning may help prevent falls and injuries or facilitate perception of useful information, supporting adaptive regulation movement.

Those of ordinary skill in the art will appreciate that foot and ankle characteristics particularly ankle flexibility, plantar tactile sensation, and strength of toe plantar flexor muscles are significant independent predictors of balance and functional ability in older people. The features of the present invention improve leg strength, flexibility, and proprioception, and augment foot plantar sensation, which may be beneficial in improving mobility and reducing fall risk. Plantar sensitivity is an important information source related to balance control as it codifies the changes in pressure under the feet, especially during gait. The sensory information reaches the brain, which senses body position and, if necessary, generates postural reflexes to maintain an upright position. Unfortunately, reduced number of foot mechanoreceptors and the increase in vibrational excitation threshold of the plantar cutaneous mechanoreceptor due to aging are considering factors that adversely affect balance changes in older adults. A target with a textured surface helps train proper gait and, hence, trains a patient's somatosensory system and decrease their visual dependence for balance. Stepping to a textured footprint can provide somatosensory feedback for foot position in three planes (width, length, and height) rather than one plane (i.e. line on the floor). Varying target width, length, and height of step challenges gait.

The target may be comprised of different surface textures so that the user can identify which portion—front, back, left, right, middle—of the target has been touched. For example, the target may be texturally divided fore/aft and left/right. The target may alternatively be divided into zones that do not correspond with the target's front, back, left, right, or middle. Different zones or portions may be the same texture. For example, the entire front portion and the entire back portion may be of different textures, which would help the patient ascertain heel to toe contact. In other embodiments, the sides or target boundary may possess a texture different from that of the mat so that the patient can ascertain how much of their foot is in the correct, targeted location. Such features allow the therapist teach tactile awareness. As one of ordinary skill in the art will appreciate, different zones or target portions may emit different sounds, vibrations, or visual indicators. For example, an auditory component at the forefoot and a different auditory component of the rear foot will promote the rocker foot heel-to-toe mechanics and cues for center of pressure.

The target need not be flat and may be inclined towards the front, back, or lateral sides. Further, embodiments of the present invention provide targets of varied heights and foam densities to challenge the vestibular system. For example, the targets of some embodiments of the present invention are designed to promote the correct gait mechanics for step height to adapt to walk on all terrains, wherein height differentials may be achieved by varying the target height relative to the mat. Varying step heights relative to the mat or between adjacent targets challenges the patient's vestibular system and they will be forced to adapt balance. Further, altering step height, gives the patient the opportunity to practice hip and stepping strategies. Thus, embodiments of the present invention allow patients to adapt their balance to different surfaces, heights, densities and transition from one surface to another to provide sensory re-weighting In addition, the auditory, tactile, or other type of stimulus contemplated herein train symmetry of movement.

The auditory cue may be paired with a visual cue, such as a light directed to the patient's eyes, which ideally are not focused on the mat. The patient could be provided with glasses that would wirelessly receive a signal from the target or mat with respect to the nature and quality of target contact, i.e., strength, percent of foot on the target, etc. The glasses frame or lens may illuminate or provide other signals, such as in a heads-up display, indicating the nature and quality of the step.

As alluded to above, other embodiments of the present invention employ devices that allow the target to vibrate when contacted. The vibration pattern or strength may be used to indicate the nature and quality of target contact—percent of footprint contacted, side of footprint contacted, whether the footprint was contacted at the four or aft, etc. Again, one of ordinary skill in the art will appreciate that visual, tactile, auditory, or vibrational feedback may be used alone or in combination or sub-combinations without departing from the scope of the invention. The target may also provide information with respect to force applied by using force plates, force sensors, spring scales sensors, and the like.

Targets that provide feedback, be it auditory, visual, tactile, or combination thereof, reduces the verbal cues to the patient, which is beneficial especially for patients that have difficulty or cannot process multi-step commands. Many closed-loop approach devices, such as wearable devices, are primarily configured to collect data and analyze gait, but most use only a visual system as a method for providing feedback during training. These systems rely on computer screens, such as provided by iPods®, or other similar devices. Relying on primarily on visual feedback is not ideal as it may confuse some patients by taking their attention away from the task at hand, and can be problematic with patients that have trouble following multistep commands. Further, many older patients, or those with cognitive impairments, have difficulty with some of the newer technology and may become frustrated with setting up and correctly using the same.

It is yet another aspect of some embodiments of the present invention to provide immediate feedback to the therapist or patient, which gives the ability to focus patient attention and enhance gait mechanics, weight shift, and balance performance. Therapists can address each phase of gait with somatosensory or auditory feedback described below. Hip position at terminal gait stance, foot pre-swing angle, and step length symmetry are addressed with immediate feedback rather than a therapist's verbal cues after the movement pattern occurs. Accordingly, this aspect, alone or with other aspects of the present invention described herein, fulfills the recognized need to train balance within the function of gait and stepping with an emphasis on foot placement while adapting to various surfaces.

It is another aspect of some embodiments of the present invention to incorporate targets on a moving surface. For example, the mat may be replaced by a treadmill belt that includes a plurality of selectively movable target locations, which may be textured. Such an embodiment allows multiple gait steps to be analyzed, and would most often be used for patients of advanced skill.

It is another aspect of some embodiments of the present invention to provide a smart system for analyzing gait and balance. That is, the mat of some embodiments of the present invention may include embedded electronics, for example, a network of wires, pressure sensors, or piezoelectric sensors, accelerometers, etc., that communicate with a central hub. Such features are mentioned in U.S. Patent Application Publication No. 2015/0364059 to Marks et al. and WIPO Publication Nos. WO0108755 to Granville and WO87/01574 to Bugarini, the entire disclosure of each is incorporated by reverence herein. The central hub would receive data from the network of embedded sensors and wired or wirelessly forward the gathered data to a remote location or the patient's computer or smart phone, for example. In this way, a therapist can monitor patient progress remotely and provide real-time or delayed feedback to the patient. The patient using the smart phone or home computer would also be able to receive real-time feedback on his or her progress and could, thus, alter their training quickly to address issues. The selectively-positionable targets of this embodiment of the present invention can also include technology that allows the mat to "know" where the targets have been placed, e.g., the targets and the mat can communicate. This positioning data is also routed to the hub for processing. "Smart" targets could also include sensors such as pressure pads and the like, which provide information to the patient or therapist. In some embodiments of the present invention, the mat includes a plurality of light elements wherein the therapist using a pre-conceived program would light up portions of the mat to indicate the preferred target placement location that corresponds with predetermined therapy routine. The therapist could, of course, initiate lighted target placement locations remotely.

In operation, targets are attached to the mat at various locations via hook/loop fasteners. The targets can be correctly positioned by using the measurement tool printed at least one edge of the mat. Therapist and patients can position targets in any fashion to dictate step length and spacing. Type and location of target can also be used to vary step height and a specific balance system. For example, a spiked target texture will challenge the patient's somatosensory system, and foam incorporated in the targets will challenge the patient's vestibular system. Stepping onto varied textures and foam densities challenges the ability to adapt balance during gait. Targets with auditory cues can provide input for symmetry of stepping and heel-toe rocker foot mechanics during gait. The use of a vertical-wall mounted mat with targets allows the incorporation of reaching activities that activate the patient's hips while reaching forward, high, or low. The incorporation of visual exercises, by use of an eye chart, for example, positioned on the wall mat also tasks the patient's vestibular ocular centers.

It is another aspect of embodiments of the present invention to provide a system for assessing a patient's gait and balance, comprising: a mat having a plurality of connection areas, the mat having an upper surface, a first edge, a second edge, a first lateral edge, and a second lateral edge; a measurement device interconnected to at least one of the first edge, the second edge, the first lateral edge, and the second lateral edge; a plurality of targets, wherein each target is comprised of a base portion interconnected to a top portion, the base portion having at least one recesses that houses a sound-producing member; wherein the plurality of targets are configured to selectively interconnect to the plurality of connection areas; and wherein the sound-producing member emits an audible cue when contacted by the patient's foot, the audible cue serving as feedback to the patient.

It is still yet another aspect of embodiments of the present invention to provide a system for assessing a patient's gait and balance, comprising: a mat having a plurality of connection areas, the mat having an upper surface, a first edge, a second edge, a first lateral edge, and a second lateral edge; a plurality of selectively positionable targets, each having a feedback-producing element; wherein the plurality of targets are configured to selectively interconnect to the plurality of connection areas; and wherein the feedback-producing member emits a signal when contacted by the patient's foot.

It is another aspect of embodiments of the present invention to provide a method of assessing a patient's gait and balance, comprising: providing a walking surface having a plurality of connection areas; providing a plurality of targets, wherein each target is comprised of a base portion interconnected to a top portion, the base portion having at least one recesses that houses a sound-producing member; selectively interconnecting the plurality of targets to the plurality of connection areas; stepping on the at least one of the plurality of targets; and issuing a sound from the sound-producing member if the patient contacts the at least one of the plurality of targets in a prescribed manner.

Further aspects of the present invention are provided in the following embodiments:

A system for assessing a patient's gait and balance, comprising: a mat having a plurality of connection areas, the mat having an upper surface, a first edge, a second edge, a first lateral edge, and a second lateral edge; a measurement device interconnected to at least one of the first edge, the second edge, the first lateral edge, and the second lateral edge; a plurality of targets, wherein each target is comprised of a base portion interconnected to a top portion, the base portion having at least one recesses that houses a sound-producing member; wherein the plurality of targets are configured to selectively interconnect to the plurality of connection areas; and wherein the sound-producing member emits an audible cue when contacted by the patient's foot, the audible cue serving as feedback to the patient.

A system for assessing a patient's gait and balance, comprising: a mat having a plurality of connection areas, the mat having an upper surface, a first edge, a second edge, a first lateral edge, and a second lateral edge; a measurement device interconnected to at least one of the first edge, the second edge, the first lateral edge, and the second lateral edge; a plurality of targets, wherein each target is comprised of a base portion interconnected to a top portion, the base portion having at least one recesses that houses a sound-producing member; wherein the plurality of targets are configured to selectively interconnect to the plurality of connection areas; wherein the sound-producing member emits an audible cue when contacted by the patient's foot, the audible cue serving as feedback to the patient; and wherein the top portion of at least one of the plurality of targets possesses a textured surface that is tactily distinct from the texture of the upper surface of the mat.

A system for assessing a patient's gait and balance, comprising: a mat having a plurality of connection areas, the mat having an upper surface, a first edge, a second edge, a first lateral edge, and a second lateral edge; a measurement device interconnected to at least one of the first edge, the second edge, the first lateral edge, and the second lateral edge; a plurality of targets, wherein each target is comprised of a base portion interconnected to a top portion, the base portion having at least one recesses that houses a sound-producing member; wherein the plurality of targets are configured to selectively interconnect to the plurality of connection areas; wherein the sound-producing member emits an audible cue when contacted by the patient's foot, the audible cue serving as feedback to the patient; and wherein the plurality of targets comprises a first target and a second target, wherein the texture of the top portion of the first target is different from the texture of the top portion of the second target.

A system for assessing a patient's gait and balance, comprising: a mat having a plurality of connection areas, the mat having an upper surface, a first edge, a second edge, a first lateral edge, and a second lateral edge; a measurement device interconnected to at least one of the first edge, the second edge, the first lateral edge, and the second lateral edge; a plurality of targets, wherein each target is comprised of a base portion interconnected to a top portion, the base portion having at least one recesses that houses a sound-producing member; wherein the plurality of targets are configured to selectively interconnect to the plurality of connection areas; wherein the sound-producing member emits an audible cue when contacted by the patient's foot, the audible cue serving as feedback to the patient; and wherein the plurality of targets comprises a first target and a second target, wherein the thickness the first target is different from the thickness of the second target.

A system for assessing a patient's gait and balance, comprising: a mat having a plurality of connection areas, the mat having an upper surface, a first edge, a second edge, a first lateral edge, and a second lateral edge; a measurement device interconnected to at least one of the first edge, the second edge, the first lateral edge, and the second lateral edge; a plurality of targets, wherein each target is comprised of a base portion interconnected to a top portion, the base portion having at least one recesses that houses a sound-producing member; wherein the plurality of targets are configured to selectively interconnect to the plurality of connection areas; wherein the sound-producing member emits an audible cue when contacted by the patient's foot, the audible cue serving as feedback to the patient; and wherein at least one of the plurality of targets possesses an upper surface, the majority thereof is not parallel to the upper surface of the mat when the at least one of the plurality of targets is interconnected to the mat.

A system for assessing a patient's gait and balance, comprising: a mat having a plurality of connection areas, the mat having an upper surface, a first edge, a second edge, a first lateral edge, and a second lateral edge; a measurement device interconnected to at least one of the first edge, the second edge, the first lateral edge, and the second lateral edge; a plurality of targets, wherein each target is comprised of a base portion interconnected to a top portion, the base portion having at least one recesses that houses a sound-producing member; wherein the plurality of targets are configured to selectively interconnect to the plurality of connection areas; wherein the sound-producing member emits an audible cue when contacted by the patient's foot, the audible cue serving as feedback to the patient; and wherein the plurality of connection areas are loop strips configures to selectively interconnect to corresponding connection devices provided on bottom surfaces of the plurality of target, wherein the plurality of targets may be positioned in a random or pre-defined fashion.

A system for assessing a patient's gait and balance, comprising: a mat having a plurality of connection areas, the mat having an upper surface, a first edge, a second edge, a first lateral edge, and a second lateral edge; a measurement device interconnected to at least one of the first edge, the second edge, the first lateral edge, and the second lateral edge; a plurality of targets, wherein each target is comprised of a base portion interconnected to a top portion, the base portion having at least one recesses that houses a sound-producing member; wherein the plurality of targets are configured to selectively interconnect to the plurality of connection areas; wherein the sound-producing member emits an audible cue when contacted by the patient's foot, the audible cue serving as feedback to the patient; and wherein the top portion of the plurality of targets employs an upper surface comprising at least two distinct textures.

A system for assessing a patient's gait and balance, comprising: a mat having a plurality of connection areas, the mat having an upper surface, a first edge, a second edge, a first lateral edge, and a second lateral edge; a measurement device interconnected to at least one of the first edge, the second edge, the first lateral edge, and the second lateral edge; a plurality of targets, wherein each target is comprised of a base portion interconnected to a top portion, the base portion having at least one recesses that houses a sound-producing member; wherein the plurality of targets are configured to selectively interconnect to the plurality of connection areas; wherein the sound-producing member emits an audible cue when contacted by the patient's foot, the audible cue serving as feedback to the patient; and wherein the base portion comprises a first recess for the receipt of a first sound-producing member and a second recess for the receipt of a second sound-producing member.

A system for assessing a patient's gait and balance, comprising: a mat having a plurality of connection areas, the mat having an upper surface, a first edge, a second edge, a first lateral edge, and a second lateral edge; a measurement device interconnected to at least one of the first edge, the second edge, the first lateral edge, and the second lateral edge; a plurality of targets, wherein each target is comprised of a base portion interconnected to a top portion, the base portion having at least one recesses that houses a sound-producing member; wherein the plurality of targets are configured to selectively interconnect to the plurality of connection areas; wherein the sound-producing member emits an audible cue when contacted by the patient's foot, the audible cue serving as feedback to the patient; and wherein the target is shaped as a human foot, and wherein the first recess is located adjected a toe portion of the target and the second recess is positioned adjacent to a heel portion of the target, and wherein the top portion conceals the first recess, the second recess, the first sound-producing member, and the second sound-producing member.

A system for assessing a patient's gait and balance, comprising: a mat having a plurality of connection areas, the mat having an upper surface, a first edge, a second edge, a first lateral edge, and a second lateral edge; a plurality of selectively positionable targets, each having a feedback-producing element; wherein the plurality of targets are configured to selectively interconnect to the plurality of connection areas; wherein the feedback-producing member emits a signal when contacted by the patient's foot; and wherein the signal is at least one of a sound, a message to a data gathering device associated with the mat, a message to a remote data gathering device, a vibration, and a signal that produces a visual cue.

A system for assessing a patient's gait and balance, comprising: a mat having a plurality of connection areas, the mat having an upper surface, a first edge, a second edge, a first lateral edge, and a second lateral edge; a plurality of selectively positionable targets, each having a feedback-producing element; wherein the plurality of targets are configured to selectively interconnect to the plurality of connection areas; wherein the feedback-producing member emits a signal when contacted by the patient's foot; and wherein the mat includes a measurement device interconnected to at least one of the first edge, the second edge, the first lateral edge, and the second lateral edge.

A system for assessing a patient's gait and balance, comprising: a mat having a plurality of connection areas, the mat having an upper surface, a first edge, a second edge, a first lateral edge, and a second lateral edge; a plurality of selectively positionable targets, each having a feedback-producing element; wherein the plurality of targets are configured to selectively interconnect to the plurality of connection areas; wherein the feedback-producing member emits a signal when contacted by the patient's foot; and wherein the top portion of at least one of the plurality of targets possesses a textured surface that is tactily distinct from the texture of the upper surface of the mat.

A system for assessing a patient's gait and balance, comprising: a mat having a plurality of connection areas, the mat having an upper surface, a first edge, a second edge, a first lateral edge, and a second lateral edge; a plurality of selectively positionable targets, each having a feedback-producing element; wherein the plurality of targets are configured to selectively interconnect to the plurality of connection areas; wherein the feedback-producing member emits a signal when contacted by the patient's foot; and wherein the plurality of targets comprises a first target and a second target, wherein at least one of the texture of the top portion of the first target is different from the texture of the top portion of the second target and the thickness the first target is different from the thickness of the second target.

A system for assessing a patient's gait and balance, comprising: a mat having a plurality of connection areas, the mat having an upper surface, a first edge, a second edge, a first lateral edge, and a second lateral edge; a plurality of selectively positionable targets, each having a feedback-producing element; wherein the plurality of targets are configured to selectively interconnect to the plurality of connection areas; wherein the feedback-producing member emits a signal when contacted by the patient's foot; and wherein the plurality of targets comprises a first target and a second target, wherein at least one of the texture of the top portion of the first target is different from the texture of the top portion of the second target and the thickness the first target is different from the thickness of the second target, and wherein at least one of the first target and the second target possesses an upper surface, the majority thereof is not parallel to the upper surface of the mat.

A system for assessing a patient's gait and balance, comprising: a mat having a plurality of connection areas, the mat having an upper surface, a first edge, a second edge, a first lateral edge, and a second lateral edge; a plurality of selectively positionable targets, each having a feedback-producing element; wherein the plurality of targets are configured to selectively interconnect to the plurality of connection areas; wherein the feedback-producing member emits a signal when contacted by the patient's foot; and wherein the plurality of connection areas are loop strips configures to selectively interconnect to corresponding connection devices provided on bottom surfaces of the plurality of target, wherein the plurality of targets may be positioned in a random or pre-defined fashion.

A system for assessing a patient's gait and balance, comprising: a mat having a plurality of connection areas, the mat having an upper surface, a first edge, a second edge, a first lateral edge, and a second lateral edge; a plurality of selectively positionable targets, each having a feedback-producing element; wherein the plurality of targets are configured to selectively interconnect to the plurality of connection areas; wherein the feedback-producing member emits a signal when contacted by the patient's foot; and wherein the top portion of the plurality of targets employs an upper surface comprising at least two distinct textures.

A system for assessing a patient's gait and balance, comprising: a mat having a plurality of connection areas, the mat having an upper surface, a first edge, a second edge, a first lateral edge, and a second lateral edge; a plurality of selectively positionable targets, each having a feedback-producing element; wherein the plurality of targets are configured to selectively interconnect to the plurality of connection areas; wherein the feedback-producing member emits a signal when contacted by the patient's foot; and wherein each target is comprised of a base portion interconnected to a top portion, the base portion having a first recess for the receipt of a first feedback-producing mechanism and a second recess for the receipt of a second feedback-producing mechanism.

A system for assessing a patient's gait and balance, comprising: a mat having a plurality of connection areas, the mat having an upper surface, a first edge, a second edge, a first lateral edge, and a second lateral edge; a plurality of selectively positionable targets, each having a feedback-producing element; wherein the plurality of targets are configured to selectively interconnect to the plurality of connection areas; wherein the feedback-producing member emits a signal when contacted by the patient's foot; and wherein the first feedback-producing member produces a first signal and the second feedback-producing member produces a second signal that is different from the first signal.

Upon review the foregoing in the following, one of ordinary skill in the art will appreciate that embodiments the present invention:

1) provide visual, auditory and somatosensory feedback during any stepping, weight shift, gait or turning activity;
2) allow patients to train/practice/reproduce proper mechanics at home, the gym or in a clinic repetitively with immediate feedback if performed incorrectly;
3) allow use of sensory information from the foot and leg to be used in walking, reducing reliance on vision;
4) increase efficient use of clinic time with immediate translation from testing to treatment;
5) provide an embedded measurement tool that allows therapists to evaluate and assess using standardized tests such as the maximal step length test, and functional reach test;
6) provide a measurement tool as an objective carryover of treatment and allows monitoring of progression;
7) provides feedback for progression of the exercises;
8) are easy to use at home with enhanced feedback to increase motivation and intensity of training;
9) provides patients quick, precise instructions on how to modify movement patterns;
10) is cost effective; and/or
11) is portable and able to use in all settings: inpatient, outpatient, homecare, gyms.

Other advantages over the prior art methods and systems, although not found in the list provided above, are described herein.

Portions of the forgoing, for example, statics and data, may be found in:

1. Lesinski M, Hortobágyi T, Muehlbauer T, Gollhofer A, Granacher U. Effects of Balance Training on Balance Performance in Healthy Older Adults: A Systematic Review and Meta-analysis. Sports Medicine (Auckland, N.Z). 2015; 45:1721-1738. doi:10.1007/s40279-015-0375-y.
2. Toulotte C, Thevenon A, Fabre C. Effects of training and detraining on the static and dynamic balance in elderly fallers and non-fallers: a pilot study. Disabil Rehabil. 2006 Jan. 30; 28(2):125-33.
3. Rossi L P, Pereira R, Brandalize M, et al. The effects of a perturbation-based balance training on the reactive neuromuscular control in community-dwelling older women: a randomized controlled trial. Hum Mov. 2013; 14(3):238-246.
4. Sherrington C, Tiedemann A, Fairhall N, Close J C, Lord S R Exercise to prevent falls in older adults: an updated meta-analysis and best practice recommendations. N S W Public Health Bull. 2011 June; 22(3-4):78-83.
5. Filippo Casamassima,2, Alberto Ferrari, 1, Bojan Milosevic,2, Pieter Ginis,3 Elisabetta Farella,2,4, and Laura Rocchi1 a Wearable System for Gait Training in Subjects with Parkinson's Disease Sensors (Basel). 2014 April; 14(4): 6229-6246)
6. Fay Horak, Laurie King. Martina Mancini Role of Body-Worn Movement Monitor Technology for Balance and Gait Rehabilitation. Phys Ther. 2015 March; 95(3): 461-470.
7. Summary of the Updated American Geriatrics Society/British Geriatrics Society clinical practice guideline for prevention of falls in older persons. Panel on Prevention of Falls in Older Persons, American Geriatrics Society and British Geriatrics Society J Am Geriatr Soc. 2011 January; 59(1):148-57.
8. Moncada L V Review Management of falls in older persons: a prescription for prevention. Am Fam Physician. 2011 Dec. 1; 84(11):1267-76.
9. Robinovitch S N, Feldman F, Yang Y, Schonnop R, Lueng P M, D Sarraf T, Sims-Gould J, Loughlin M. Video capture of the circumstances of falls inelderly people residing in long-term care: An observational study. The Lancet. 2013; 381:47-54
10. Menz H, Morris M, Lord S. Foot and ankle characteristics associated withimpaired balance and functional ability in older people. J Gerontol A BiolSci Med Sci 2005; 60A:1546-52.
11. Onivald O Bretan. Plantar cutaneous sensitivity as a risk for falls in the elderly. Rev Assoc Med Bras. 2012 March-April; 58(2):132.
12. Dominic Orth, Keith Davids, Jon Wheat, Ludovic Seifer, Jarmo Liukkonen, Timo Jaakkola, Derek Ashford, Graham Kerr The Role of Textured Material in Supporting Perceptual-Motor Functions. Plosone: April 2013: Volume 8; issue 4.
13. Hatton A L, Dixon J, Rome K, Martin D (2011) Standing on textured surfaces: Effects on standing balance in healthy older adults. Age Ageing40: 363-368.
14. Maki B E, Perry S D, Norrie R G, Mcllroy W E (1999) Effect of facilitation of sensation from plantar foot-surface boundaries on postural stabilization in young and older adults. J Gerontol 54A: M281-M287).
15. Dixon J, Hatton A L, Robinson J, Gamesby-Iyayi H, Hodgson D, Rome K, Warnett R, Martin D J Effect of textured insoles on balance and gait in people with multiple sclerosis: an exploratory trial. Physiotherapy. 201 June; 100(2):142-9.
16. Hatton A L, Dixon J, Rome K, Martin D (2011) Standing on textured surfaces: Effects on standing balance in healthy older adults. Age Ageing 40:363-368.
17. Palluel E, Nougier V, Olivier I. Do spike insoles enhance postural stability and plantar-surface cutaneous sensitivity in the elderly? Age 2008; 30:53-61.
18. Preszner-Domjan A, Nagy E, Sziver E, Feher-Kiss A, Horvath G, et al. (2012) When does mechanical plantar stimulation promote sensory re-weighing: Standing on a firm or compliant surface? Eur J Appl Physiol 112: 2979-2987.
19. Chaikeeree N, Saengsirisuwan V, Chinsongkram B, Boonsinsukh R Interaction of age and foam Test for Sensory Interaction and Balance (CTSIB). Gait Posture. 2015 January; 41(1):313-5.
20. Chia-Cheng Lin, Jennica. L. Roche, Daniel P. Steed, Mark C. Musolino, Greg F. Marchetti, Gabriel R. Furman, Mark S. Redfern, Susan L. Whitney Test-retest reliability of postural stability on two different foam pads. Journal of Nature and Science, Vol. 1, No. 2, e43, 2015.
21. Gosselin G., Fagan M, Foam pads properties and their effects on posturography in participants of different weight Chiropractic & Manual Therapies 201523:2.

The Summary of the Invention is neither intended nor should it be construed as being representative of the full extent and scope of the present invention. That is, these and other aspects and advantages will be apparent from the disclosure of the invention(s) described herein. Further, the above-described embodiments, aspects, objectives, and configurations are neither complete nor exhaustive. As will be appreciated, other embodiments of the invention are possible using, alone or in combination, one or more of the features set forth above or described below. Moreover, references made herein to "the present invention" or aspects thereof should be understood to mean certain embodiments of the present invention and should not necessarily be construed as limiting all embodiments to a particular description. The present invention is set forth in various levels of detail in the Summary of the Invention as well as in the attached drawings and the Detailed Description of the Invention and no limitation as to the scope of the present invention is intended by either the inclusion or non-inclusion of elements, components, etc. in this Summary of the Invention. Additional aspects of the present invention will become more readily apparent from the Detail Description, particularly when taken together with the drawings.

BRIEF DESCRIPTION OF THE DRAWINGS

The accompanying drawings, which are incorporated in and constitute a part of the specification, illustrate embodiments of the invention and together with the general description of the invention given above and the detailed description of the drawings given below, serve to explain the principles of these inventions.

FIG. 13A is a detailed view of a pyramid texture that covers a portion or the entirety of the target;

FIG. 13B is a detailed view of a groove texture that covers a portion or the entirety of a target;

FIG. 13C is a detailed view of a turf-like texture that covers a portion or the entirety of the target;

Figures 1, 2:
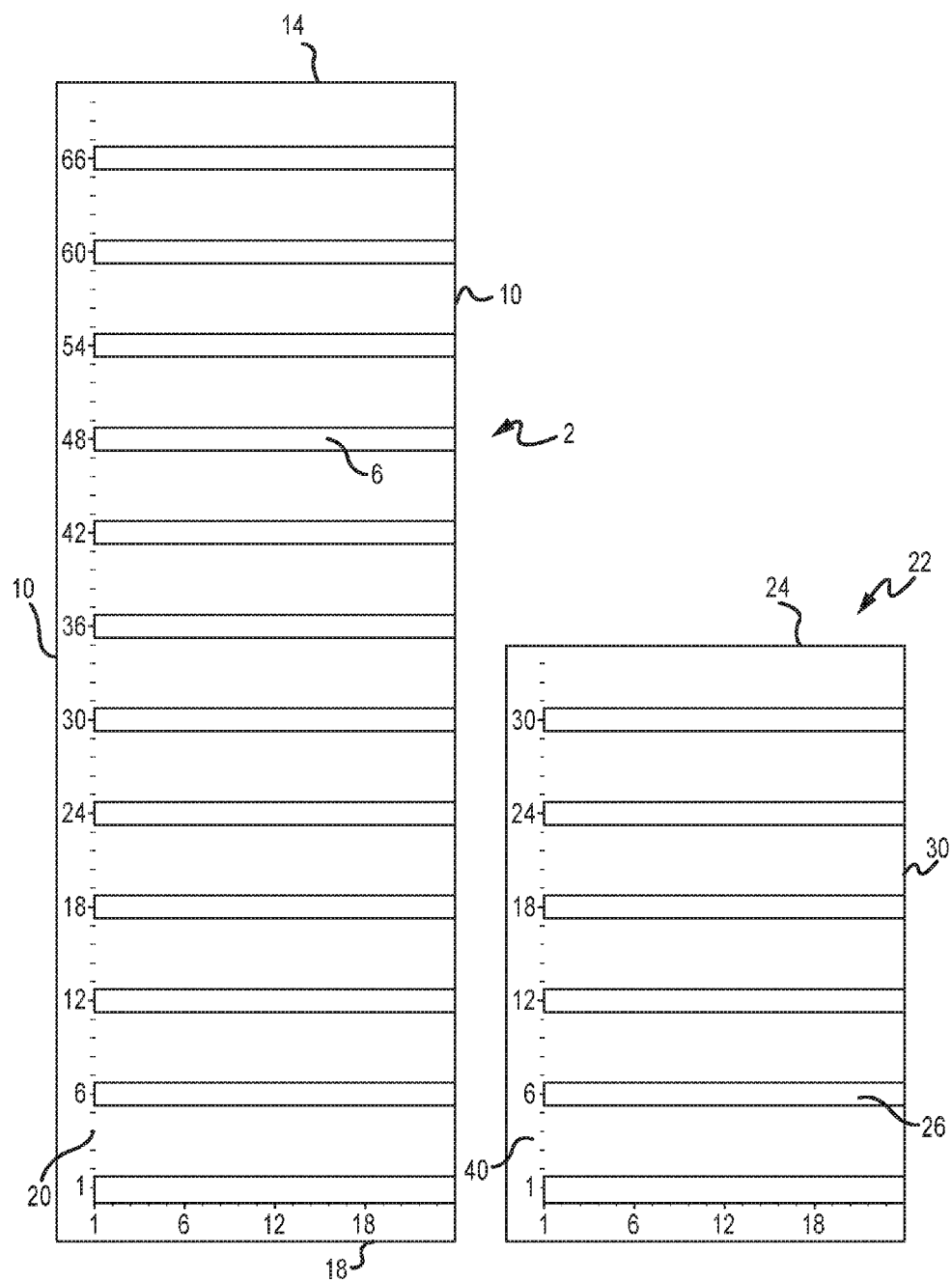
FIG. 1 is a top plan view of a floor mat of one embodiment of the present invention.
FIG. 2 is a top plan view of a wall mat of one embodiment of the present invention.
Figure 3:
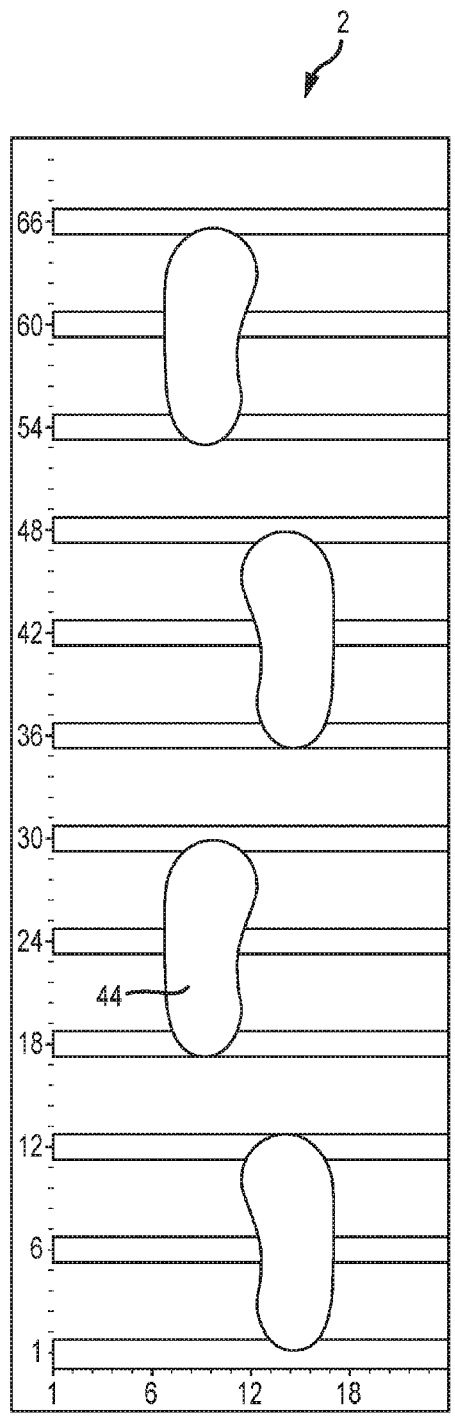
FIG. 3 is a top plan view of the floor mat with a footprint configuration for training stepping in sagittal plane.
Figure 4:
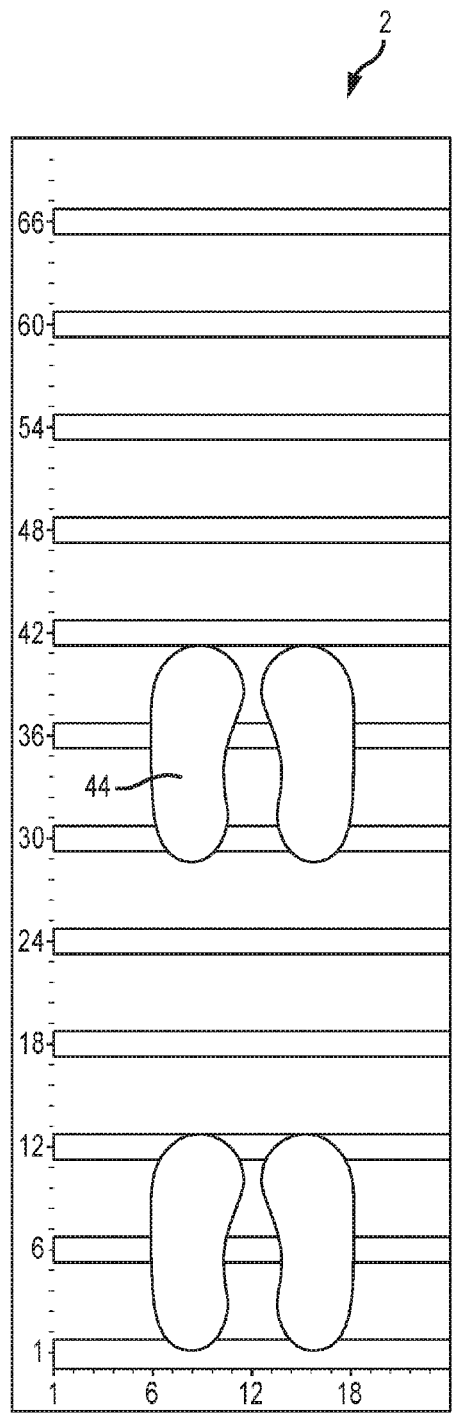
FIG. 4 is a top plan view of a floor mat with footprints for training maximal step length in the sagittal plane, stepping forwards and backwards.
Figure 5:
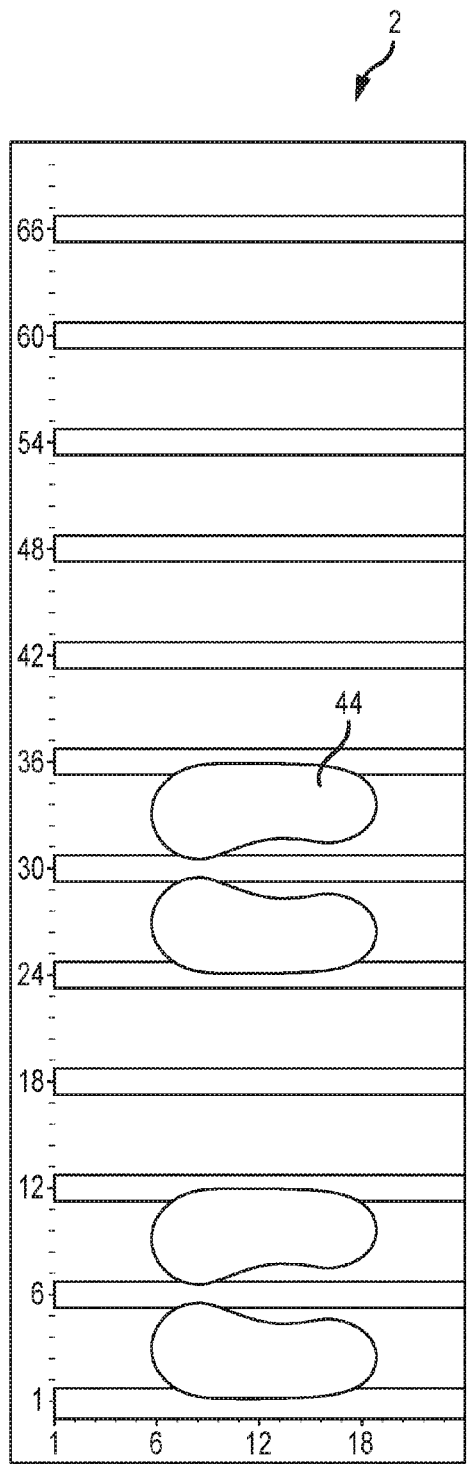
FIG. 5 is a top plan view of a floor mat for training stepping sideways.
Figure 6:
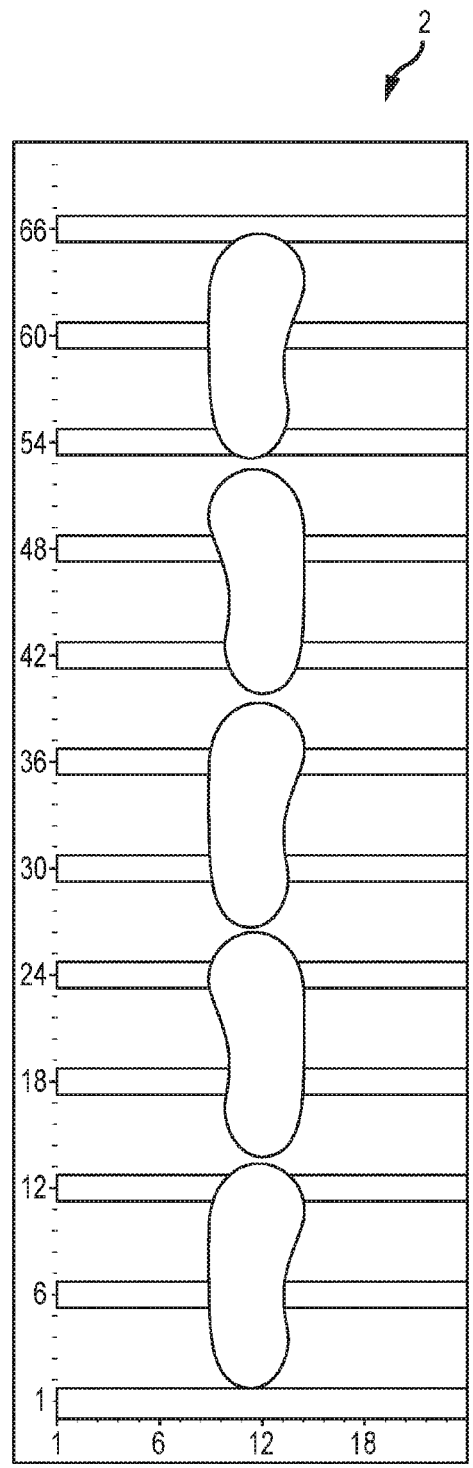
FIG. 6 is a top plan view of a floor mat for training tandem walking.
Figure 7:
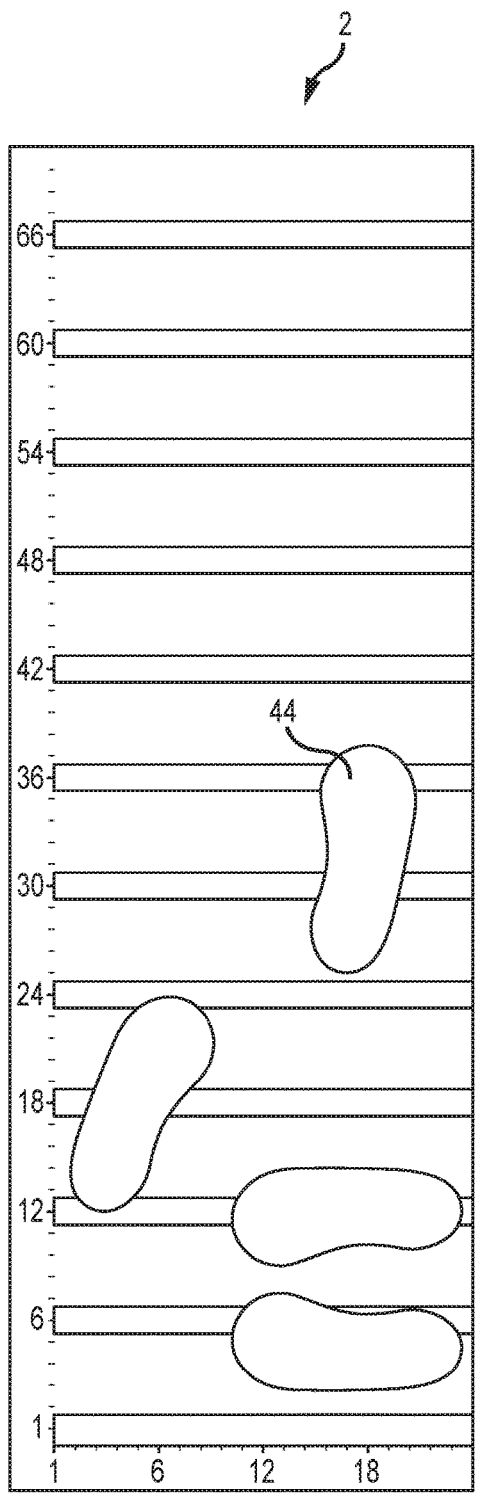
FIG. 7 is a top plan view of a floor mat for training stepping in the transverse plane to assist stepping and weight shift during turning.
Figure 8:
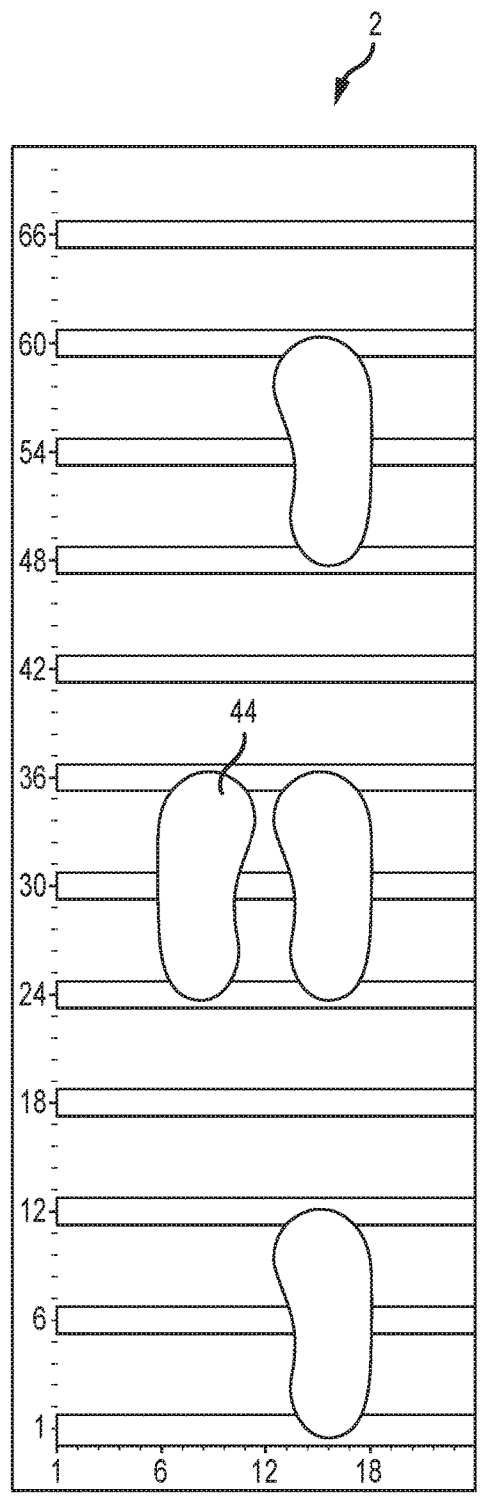
FIG. 8 is a top plan view of a floor mat for training stepping forward and back with one foot to focus on left stance phase of gait and right swing phase and ankle/foot mechanics from push off to heel strike.

To assist in the understanding of one embodiment of the present invention the following list of components and associated numbering found in the drawings is provided herein:

| # | Component |
|---|---|
| 2 | Mat |
| 6 | Loop strip |
| 10 | Lateral edge |
| 14 | First edge |
| 18 | Second edge |
| 20 | Measurement tool |
| 22 | Mat |
| 26 | Line |
| 30 | Lateral edge |
| 34 | First edge |
| 38 | Second edge |
| 40 | Measurement tool |
| 44 | Target |
| 48 | Base layer |
| 52 | Recess |
| 56 | Upper layer |
| 60 | Sound-producing element |

It should be understood that the drawings are not necessarily to scale. In certain instances, details that are not necessary for an understanding of the invention or that render other details difficult to perceive may have been omitted. It should be understood, of course, that the invention is not necessarily limited to the embodiments illustrated herein.

DETAILED DESCRIPTION

FIG. 1 shows a mat 2 of one embodiment of the present invention. The mat 2 may be the same size and shape of as a common yoga mat—about 72 to 80 inches long, by about 24 inches wide, and about 0.25 inches thick. The mat length must be long enough to allow a patient to complete one gait cycle, i.e. a double step. One of ordinary skill the art will appreciate that longer mats allow more than one gait cycle also contemplated by this disclosure. The mat 2 includes loop strips 6 positioned along the length of the mat, about every 6 inches, that targets and provides visual reference so steps can be analyzed. The loop strips 6 also selectively receive targets placed at preferred locations. One of ordinary skill the art will appreciate that the targets may be selectively interconnected to the mat by other methods, such as by magnets, snaps, clasps, or other selectively interconnecting mechanisms. Although the loop strips are shown orthogonal to the mat's lateral edges 10 and parallel to the mat's first edge 14 and second edge 18, they could be angled relative to the lateral edges 10. Further, a loop strip grid may be provided.

The mat also includes a measurement tool 20 printed or fixed along at least one of the first edge 14, the second edge 18, or one of the lateral edges 10. The measurement tool allows stance position measurement and helps locate the targets. The mat may include measurement indicia on at least two orthogonal mat sides to allow step length and width distance assessment.

FIG. 2 shows a mat 22 that may be shorter than the floor showing FIG. 1. Here, the mat 22 is designed to be attached to a door or wall via selective interconnection mechanisms, grommets, straps, or any other device that allows the mat 22 to hang vertically. In this fashion the mat 22 can be positioned at various heights. Further, the mat 22 is hung so the measurement device is vertical or horizontal. Lines 26, which can be loop strips, with high contrast with different spatial frequencies will assist with optokinetic stimulation.

Figure 14:
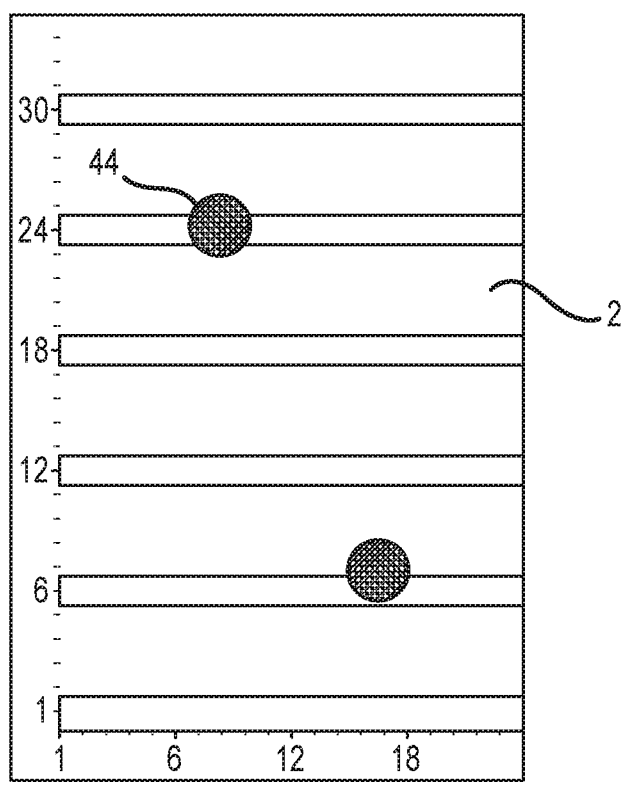
FIG. 14 is a top elevation view of mat that employs circle targets.

FIGS. 3-9 show examples of how targets 44 can be placed in various configurations for stepping and balance training. Here, the targets 44 are footprint shaped. One of ordinary skill in the art will appreciate that the targets 44 may be of any shape, such as circles as shown in FIG. 14. The targets 44 may be of the same texture or each adjacent target 44 may be of different textures. Any combination of textures is contemplated. For example, two adjacent targets may have the same texture wherein the third target has a different texture and so forth. It follows that the targets may have different heights, be comprised a different foams and materials, etc. As described above, targets 44 that produce auditory cues may also be used to provide gait mechanics or heel to toe feedback.

Figure 9:
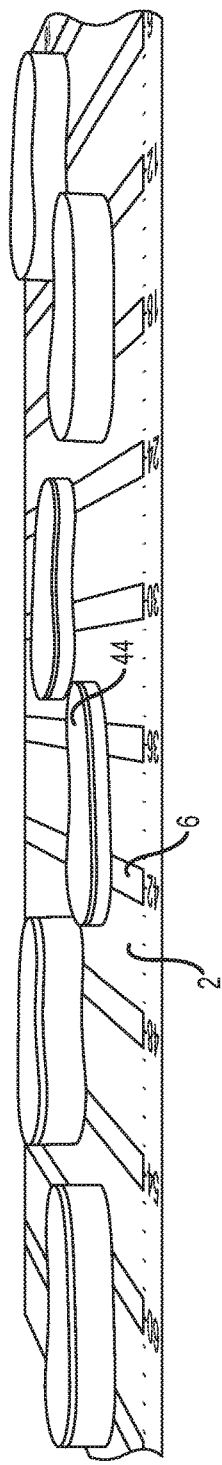
FIG. 9 is a side perspective view of a mat and a plurality of targets of various thicknesses.

FIG. 9 shows a plurality of targets 44 of varied thicknesses positioned on a mat 2 of one embodiment of the present invention. The targets 44 may be made of a combination of resilient material, such as foam, and stiff materials. The therapist may provide a treatment protocol that requires the patient to step on targets of various thicknesses so they can learn to ascertain surface height changes from a target to another.

Figure 10:
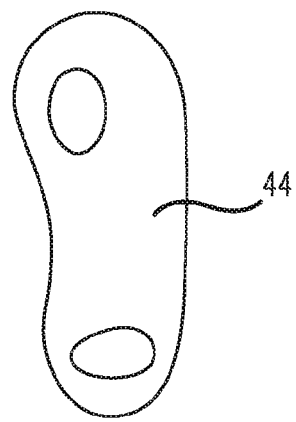
FIG. 10 is a top plan view of a footprint shaped target that has sound producing elements at the forward and heel portions.
Figure 11:
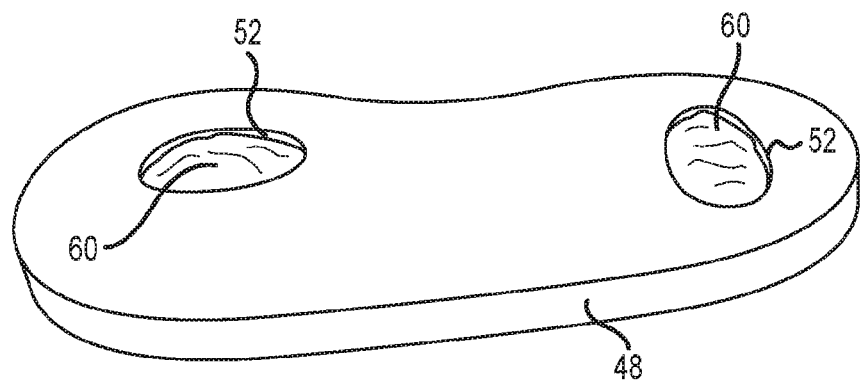
FIG. 11 is a side perspective view of FIG. 10, wherein a top cover portion has been removed for clarity.
Figure 12:
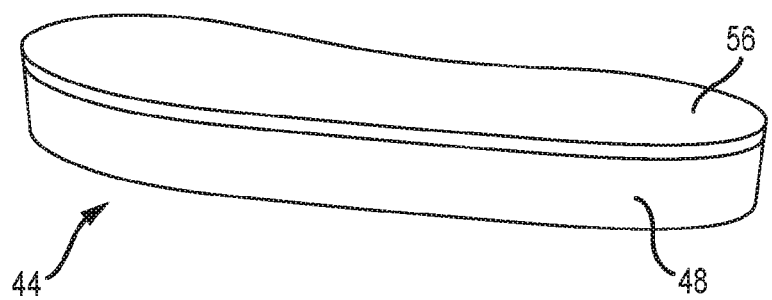
FIG. 12 is a side perspective view of FIG. 10.

FIGS. 10-12 show a footprint shaped target 44 of one embodiment of the present invention. Here, a foam base 48 that is about 0.75 inches thick is employed that has at least two locations 52—inserts, recesses, pouches, etc.—for the receipt of clickers or other sound-producing mechanisms. The heel insert may be in the shape of a teardrop and the forefoot insert may be an oval shape so the clicker can be turned facing towards the top or bottom of the footprint to accommodate the patient's foot for easier clicker activation. The target may be constructed of the foam base layer 48 and a foam upper layer 56, which may be textured. The sound-producing elements 60 are provided in the recesses 52 in the base layer. The base member includes a selectively interconnecting member, such as hook/loop fasteners that selectively receive and retain corresponding interconnection mechanisms on the upper layer 56.

Figure 13:
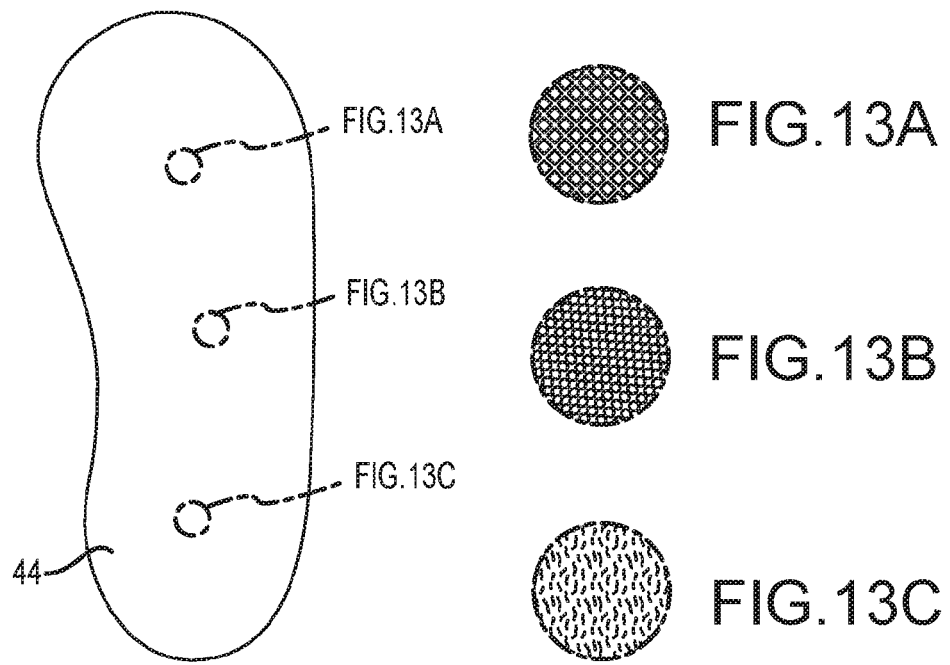
FIG. 13 is a top plan view of a target.
Figure 13D:
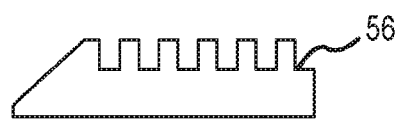
FIG. 13D is a side elevation view of a texture pattern of another embodiment of the present invention.

FIGS. 13-13D show a target 44 with various textures it can incorporate. The target 44 may be substantially flat wherein no texture is employed. Alternatively, and often beneficial to rehabilitation, the target 44 may be covered, or covered in selected areas, with a textured surface. Furthermore, a target may include various textures to define different areas of the target, the boundaries of the target, etc.

For example, detailed views 13A-C show some textures contemplated by embodiments the present invention. Those of ordinary skill the art will appreciate various other textures may be employed without departing from the scope of the invention. The location of the ends of the leader lines associated with FIGS. 13A-13C are not meant to indicate the exact location of the textured area. FIG. 13A is composed of pyramid shapes formed in lightweight EVA (ethylene vinyl acetate) foam. In one embodiment, the pyramid peaks are spaced about 2.5 mm apart and are about 3 mm high.

FIG. 13B shows a texture composed of crisscrossed, raised portions, which may be formed of small, soft fingers. FIG. 13C shows a turf-like texture made of polyethylene fibers (denier 10,800/4,500, pile height: tufted at 1.75-inch stabilized duel layer primary backing, secondary backing: 20 oz. HD urethane coating).

The textures contemplated herein may be made of recycled rubber materials. And, as mentioned above, the textured upper target portions may include a selectively interconnection mechanism, such as hook and loop fasteners (i.e., Velcro®) that allow the upper portion to be selectively interconnected to base layers comprising a foam or other material. The foam used by some embodiments of the present invention possess an indentation force deflection (IFD) of about 95, which equates to a density of 1.8 pounds per cubic foot (PCF). The base portion may be molded or include a corresponding selective interconnection system, i.e. the hook of a hook and loop fastener system. By contrast, the upper layer may have an IFD of about 61 with the density of 2.5 PCF. In practice, the top, textured layer of the target may be positioned on the mat alone, or in combination with the foam base layer.

FIG. 13D shows a side elevation view of the top, textured target layer of one embodiment of the present invention. Here, the top layer is about 0.375-inch-thick, wherein the apex of the textured surface is supported by a sub-base interconnected to the base layer of the target or directly to the mat.

The textured surface and the "control" mat surface may emulate textures found in an accompanying children's book. The book will include, for example, illustrations of how animals and humans balance and move and corresponding exercises. Animal sounds may be the auditory cue so the child or mentally-impaired patient may match the sound with the texture. A child must feel the texture in the book then note the same on the floor or wall mat.

FIG. 14 is yet another top plan view of the mat 2 of one embodiment of the present invention employed circle-shaped targets 44 instead of footprint shaped targets. One purpose of this figure is to illustrate that targets 44 may be of any shape without departing from the scope of the invention. Here, the targets 44 are spaced in such a way to help train individuals to master or improve reaching their hand to target to improve balance during reaching tasks.

While various embodiments of the present invention have been described in detail, it is apparent that modifications and alterations of those embodiments will occur to those skilled in the art. It is to be expressly understood that such modifications and alterations are within the scope and spirit of the present invention, as set forth in the following claims. Further, it is to be understood that the invention(s) described herein is not limited in its application to the details of construction and the arrangement of components set forth in the preceding description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

What is claimed is:

1. A system for assessing a patient's gait and balance, comprising:
    a mat having a plurality of connection areas, the mat having an upper surface, a first edge, a second edge, a first lateral edge, and a second lateral edge;
    a measurement device interconnected to at least one of the first edge, the second edge, the first lateral edge, and the second lateral edge;
    a plurality of targets, wherein each target is comprised of a base portion interconnected to a top portion, the base portion having a recess that houses a sound-producing member;
    wherein the plurality of targets are configured to selectively interconnect to the plurality of connection areas;
    wherein the sound-producing member emits an audible cue when contacted by the patient's foot, the audible cue serving as feedback to the patient; and
    wherein the plurality of connection areas are strips comprised of a first portion of a hook and loop connection system configured to selectively interconnect to a corresponding second portion of the hook and loop connection system provided on a bottom surface of the base portions of the plurality of targets, and wherein the plurality of targets is selectively interconnected to the plurality of connection areas in a random or pre-defined arrangement using the hook and loop connection system.

2. The system of claim 1, wherein the top portion of at least one of the plurality of targets possesses a textured surface that is tactilely distinct from the texture of the upper surface of the mat.

3. The system of claim 1, wherein the plurality of targets comprises a first target and a second target, wherein the texture of the top portion of the first target is different from the texture of the top portion of the second target.

4. The system of claim 1, wherein the plurality of targets comprises a first target and a second target, wherein the thickness the first target is different from the thickness of the second target.

5. The system of claim 1, wherein at least one of the plurality of targets possesses an upper surface, wherein the majority thereof is not parallel to the upper surface of the mat when the at least one of the plurality of targets is interconnected to the mat.

6. The system of claim 1, wherein the top portion of the plurality of targets employs an upper surface comprising at least two distinct textures.

7. The system of claim 1, wherein the recess of the base portions of the plurality of targets is a first recess for the receipt of the sound-producing member, and further comprising a second recess in the base portions of the plurality of targets for the receipt of a second sound-producing member.

8. The system of claim 7, wherein the target is shaped as a human foot, and wherein the first recess is located adjacent a toe portion of the target and the second recess is positioned adjacent to a heel portion of the target, and wherein the top portion conceals the first recess, the second recess, the first sound-producing member, and the second sound-producing member.

9. A system for assessing a patient's gait and balance, comprising:
    a mat having a plurality of connection areas, the mat having an upper surface, a first edge, a second edge, a first lateral edge, and a second lateral edge;
    a plurality of selectively positionable targets, each having a feedback-producing element;
    wherein the plurality of selectively positionable targets are configured to selectively interconnect to the plurality of connection areas;
    wherein the feedback-producing member emits a signal when contacted by the patient's foot; and
    wherein the plurality of connection areas are strips comprised of a first portion of a hook and loop connection system configured to selectively interconnect to a corresponding second portion of the hook and loop connection system provided on a bottom surface of the plurality of selectively positionable targets, and wherein the plurality of selectively positionable targets is selectively interconnected to the plurality of connection areas in a random or pre-defined arrangement using the hook and loop connection system.

10. The system of claim 9, wherein the signal is at least one of a sound, a message to a data gathering device associated with the mat, a message to a remote data gathering device, a vibration, and a signal that produces a visual cue.

11. The system of claim 9, wherein the mat includes a measurement device interconnected to at least one of the first edge, the second edge, the first lateral edge, and the second lateral edge.

12. The system of claim 9, wherein a top surface of at least one of the plurality of selectively positionable targets possesses a textured surface that is tactilely distinct from the texture of the upper surface of the mat.

13. The system of claim 9, wherein the plurality of selectively positionable targets comprises a first target and a second target, wherein at least one of the texture of a top surface of the first target is different from the texture of a top surface of the second target and the thickness the first target is different from the thickness of the second target.

14. The system of claim 9, wherein the plurality of selectively positionable targets comprises a first target and a second target, wherein at least one of the texture of a top surface of the first target is different from the texture of a top surface of the second target and the thickness the first target is different from the thickness of the second target, and wherein at least one of of the majority of the top surface of the first target and the majority of the top surface of the second target is not parallel to the upper surface of the mat.

15. The system of claim 9, wherein a top surface of the plurality of selective positionable targets comprises at least two distinct textures.

16. The system of claim 9, wherein each selectively positionable target is comprised of a base portion interconnected to a top portion, the base portion having a first recess for the receipt of a first feedback-producing mechanism and a second recess for the receipt of a second feedback-producing mechanism.

17. The system of claim 16, wherein the first feedback-producing member produces a first signal and the second feedback-producing member produces a second signal that is different from the first signal.

18. A method of assessing a patient's gait and balance, comprising:
provid ing a walking surface having a plurality of connection areas;
providing a plurality of targets, wherein each target is comprised of a base portion interconnected to a top portion, the base portion having at least one recess that houses a sound-producing member;
wherein the plurality of connection areas are strips comprised of a first portion of a hook and loop connection system configured to selectively interconnect to a corresponding second portion of the hook and loop connection system provided on a bottom surface of the base portions of the plurality of targets;
selectively interconnecting the plurality of targets to the plurality of connection areas;
stepping on the at least one of the plurality of targets; and
issuing a sound from the sound-producing member if the patient contacts the at least one of the plurality of targets in a prescribed manner.

* * * * *